(12) United States Patent
Selvin et al.

(10) Patent No.: US 7,829,278 B2
(45) Date of Patent: Nov. 9, 2010

(54) POLYNUCLEOTIDE BARCODING

(75) Inventors: Paul R. Selvin, Urbana, IL (US); Matthew Gordon, Urbana, IL (US); Pui-Yan Kwok, San Francisco, CA (US); Ming Xiao, Pacifica, CA (US); Ting-Fung Chan, San Francisco, CA (US)

(73) Assignees: Board of Trustees of the University of Illinois, Urbana, IL (US); Regents of the University of California, Oakland, CA (US)

( * ) Notice: Subject to any disclaimer, the term of this patent is extended or adjusted under 35 U.S.C. 154(b) by 1393 days.

(21) Appl. No.: 10/976,546

(22) Filed: Oct. 28, 2004

(65) Prior Publication Data

US 2006/0094019 A1    May 4, 2006

(51) Int. Cl.
*C12Q 1/68* (2006.01)
(52) U.S. Cl. .......................................................... 435/6

(58) Field of Classification Search ...................... None
See application file for complete search history.

(56) References Cited

U.S. PATENT DOCUMENTS 6,013,431 A * 1/2000 Soderlund et al. .............. 435/5

OTHER PUBLICATIONS

Oana et al., Biochem Biophys Res Commun, 1999, 265: 140-143.*
Nilsson et al., Science, 1994, 265: 2085-2088.*
Yildiz et al., Science, Jun. 2003, 300: 2061-2065.*

* cited by examiner

*Primary Examiner*—Ileana Popa
(74) *Attorney, Agent, or Firm*—Richard Aron Osman

(57) ABSTRACT

A polynucleotide is barcoded using a method whereby an isolated, individual polynucleotide is immobilized on a solid phase and stretched, targets are labeled using target-specific hybridization probes, and an individual label of an unamplified probe at each of the labeled targets is optically detected. The order of the labels is determined to form a barcode representation of the polynucleotide wherein the targets and their relative positions are represented.

13 Claims, 1 Drawing Sheet

POLYNUCLEOTIDE BARCODING

This invention was made with US Government support under Grant Nos DBI-02-15869 and MCB-99-84841CAR awarded by the NSF; Grant Nos. PHS 5 R01-AR44420C and PHS 5 T32-GM08276 awarded by NIH; and Grant Nos. DEFG02-91ER45439 awarded by DOE. The Government has certain rights in this invention.

FIELD OF THE INVENTION

The field of the invention is methods for barcoding polynucleotides.

BACKGROUND OF THE INVENTION

With the completion of the sequencing of the human genome the scientific community is in a position to begin studying the relationship between genetics and disease in earnest. Several groups have already embarked on the first stage of such studies, a comprehensive mapping of the SNPs and genetic markers in the human genome (Collins et al, Nature (2003) 422:835-847). Using this information, a genome-wide scan of SNPs of a population can establish potentially interesting regions of the genome associated with a particular disease (Botstein et al, Nat Genet (2003) 33:228-237). However, in such results, there will be a high incidence of false positives due to the multiple-testing problem, and a high incidence of false negatives, due to weak correlation between single SNPs and a given disease. Therefore, after this stage, it becomes necessary to reexamine the identified regions with a finer-grained mapping of genetic features to confirm the previously established relationships. In these studies, the power to detect correlations is greatly increased by comparing haplotypes of the case studies, rather than just studying SNPs (Douglas et al, Nat Genet (2001) 28:361-364).

Determination of genetic haplotypes is difficult in heterozygous diploid organisms. The technologies currently in broad use for sequencing studies are based on bulk studies of PCR products. Since these technologies genotype products which are derived from a combination of both chromosomes, they cannot distinguish SNPs which are different on different chromosomes; hence the individual's haplotype cannot be resolved at loci where the subject is heterozygous.

Some groups have circumvented this problem by physically separating the chromosomes prior to PCR (Patil et al, Science (2001) 294:1719-1723; Douglas et al, 2001) by using allele-specific PCR to amplify only one of the parent chromosomes in a heterozygous individual (Michalatos-Beloin et al, Nucl. Acids. Res. (1996) 24:4841-4843), or by single-molecule PCR (Ding and Cantor, Proc Natl Acad Sci USA (2003) 100:7449-7453). However, these cloning techniques are laborious and the PCR-based methods can only amplify short DNA fragments, which can limit their application to high-throughput haplotyping methods. Another group has shown that labeled single DNA molecules can be imaged by atomic force microscopy (AFM) (Woolley et al, Nat Biotechnol (2000) 18:760-763), but this approach requires sophisticated and expensive instrumentation not readily available to most laboratories. Other investigators have analyzed individual, allele-specifically labeled polynucleotides using capillary flow past fluorescence detectors (Goodwin et al, Curr Pharm Biotechnol (2004) 5:271-278), however haplotypes defined by more than two SNPs must be identified by the repeated typing of pairs of SNPs.

Over the past decade, technological advances have allowed biophysicists to study biological systems on a molecule-by-molecule basis, giving them the unprecedented capacity to resolve properties of complex systems that are obscured by measuring properties which are averaged over the entire ensemble. One approach to measuring properties of single molecules is through fluorescence. For instance, we have recently demonstrated the ability to localize single fluorescent molecules with very high accuracy (approximately 1.5 nm) with half-second time resolution over the course of several minutes. We refer to this technique as Fluorescence Imaging with One Nanometer Accuracy (FIONA), and have used it to investigate the processive walking of the myosin V (Yildiz et al, Science (2003) 300:2061-2065) and kinesin (Yildiz, et al. (2004) Science 303, 676-678) molecular motors labeled with Cy3. We have also shown that we can achieve similar results with a variety of different types of dyes (Snyder et al, Biophys J. (2004) 87:1776-1783; Park, H., Hanson, G., Duff, S. & Selvin, P. (2004) Journal of Microscopy) on both proteins and DNA, making FIONA a highly versatile technique.

The image of a single fluorescent molecule (often called its "point spread function", or PSF) will have a width (w), dictated by the Rayleigh diffraction limit, of $\lambda/(2 \times NA)$, where $\lambda$ is the wavelength of the emitted light, and NA is the numerical aperture of the optical system. However, the centroid of the PSF can be determined much more accurately than this. This is actually quite an intuitive result: the position of the peak of a mountain can be determined with great precision, and with an accuracy much smaller than the width. In fluorescence imaging, the centroid of the PSF can be determined to within approximately $w/\sqrt{N}$, where N is the number of collected photons (Thompson, et al. (2002) Biophys. J. 82, 2775-2783).

In FIONA, a molecule labeled with a single dye is illuminated using total internal reflection microscopy (Axelrod, D. (1989) Methods Cell Biol 30, 245-70), and the photons emitted by the dye molecule are collected by a high-numerical aperture oil objective, and imaged using a high-speed back-thinned cooled CCD camera. The images are captured with no dead time between images, creating a continuous "movie" of the molecule. Each image frame is then fit to a Gaussian distribution to determine the position of the centroid. By actively deoxygenating solutions using a glucose oxidase/catalase "cocktail" and by suppressing dye blinking with appropriate buffer conditions, we can collect approximately 10,000 photons in one half second integration from a single molecule. For red light ($\lambda \approx 150$ nm), this means we can localize molecules to within approximately 1.5 nm, as stated above.

By taking advantage of the time resolution available to FIONA and the quantal photobleaching of single dye molecules, we have shown the ability to resolve distances between single dye molecules of the same color down to 10 nm (Gordon, M. P., Ha, T. & Selvin, P. R. (2004) PNAS 101, 6462-6465). FIONA can also be used to distinguish single molecules of different colors by accurate determination of their PSF width, which should be proportional to their wavelength, according to the Rayleigh diffraction limit discussed above.

We disclose a cost-effective, high-throughput system for haplotyping based on single-molecule technologies in which isolated, individual polynucleotide molecules from diploid organisms are labeled allele-specifically with target-specific hybridization probes. Individual labels at each target allele are optically detected, and a barcode representation of the polynucleotide is formed where the alleles and their relative positions are represented. Barcoding polynucleotides according to our invention facilitates a variety of analyses, including genotyping, sequencing and haplotyping.

RELEVANT LITERATURE

We have reported aspects of the present invention in Gordon et al, Proc Nat Acad Sci (2004) 101:6462-6464; Kwok and Xiao, Hum Mutat (2004) 23:442-446; and Snyder et al, Biophys J. (2004) 87:1776-1783.

Additional relevant literature includes: Yildiz et al, Science (2003) 300:2061-2065; Conti and Bensimon, Genomics (2002) 88:135-137; Gad et al, J Med Genet (2002) 39:817-821; Goodwin et al, (2004); Jing et al, Proc Nat Acad Sci USA (1998) 95:8046-8051; Kwok, "Approaches to Molecular Haplotyping", Mutation Detection 2003, VII International Symposium on Mutations in the Genome; Michalet et al, Science (1997) 277:1518-1523; Pasero et al, Genes Dev (2002) 16:2479-2484; Qu et al, Proc Nat Acad Sci USA (2004) 101:11298-11303; Woolley et al, Nat Biotechnol (2000) 18:760-763; and Zhong et al, Proc Nat Acad Sci USA (2001) 98:3940-3945.

SUMMARY OF THE INVENTION

One aspect of the invention provides a method for barcoding a polynucleotide, comprising the steps of: a) immobilizing on a solid phase and stretching an isolated, individual polynucleotide comprising nucleotide targets; b) labeling each of the targets using a corresponding target-specific hybridization probe; and c) directly optically detecting a predetermined number of labels of each said probe, unamplified, at each of the labeled targets, and determining their order to form a barcode representation of the polynucleotide wherein the targets and their relative positions are represented.

In one embodiment of the invention, the immobilizing and stretching step comprises a technique selected from the group consisting of viscous drag, electrophoresis, optical force, and molecular combing.

In one embodiment of the invention, the labels are selected from fluorescent labels and light-scattering labels. In a preferred embodiment, the labels are fluorescent. In a particular embodiment, the labels are fluorescent, and comprise distinctly detectable fluorescent dyes. In a further embodiment, the labels are fluorescent, are attached to the probes through different linkers, and in the detection step, the labels are distinguished based on different optical influences on the labels by the different linkers. In still a further embodiment, the labels are fluorescent, are attached to the probes through different linkers, and in the detection step, the labels are distinguished based on different optical influences on the labels by the different linkers, wherein the linkers are different length carbon chains which polarize label fluorescence inversely to label length.

In one embodiment of the invention, in the labeling step, discontinuous probes are hybridized to the targets, and gap-filled with fluorescent nucleotides. In another embodiment, in the labeling step, discontinuous probes are hybridized to the targets, and gap-filled with fluorescent nucleotides, wherein a first fluorophore is used to label a subset of nucleotides A, T, G, and C; and a second fluorophore is used to label the remaining nucleotides. In a further embodiment, in the labeling step, discontinuous probes are hybridized to the targets and gap-filled with fluorescent nucleotides, wherein a distinct fluorophore is used to label each of nucleotides, A, T, G, and C.

In one embodiment of the invention, the polynucleotide comprises SNP alleles of a haplotype, the targets are the alleles, and the barcode represents the haplotype. In a further embodiment, the polynucleotide comprises SNP alleles of a haplotype, the targets are the alleles, the barcode represents the haplotype, and the labeling step comprises using a distinct fluorophore to label each of a common and a minor polymorphism of each of the alleles.

In one embodiment of the invention, in the labeling step, the probes are padlock probes.

In another embodiment of the invention, in the detecting step, the predetermined number is from 1 to 8, preferably from 1 to 4. The label number is independent of probe length. In a particular embodiment, the number is one, i.e. a single, individual label of each probe is directly, optically detected, such as with FIONA.

In another embodiment of the invention, method further comprises the step of end-labeling the polynucleotide.

In another embodiment of the invention, the method additionally comprises, prior to the detecting step, labeling the polynucleotide with a sequence non-specific dye. In a further embodiment, the method additionally comprises, prior to the detecting step, labeling the polynucleotide with a sequence non-specific dye, wherein the detecting step comprises determining the ratio of intensity of the dye on one side of a labeled target to the total dye intensity to provide a position of the labeled target as a fraction of the total length of the polynucleotide.

In another embodiment of the invention, the detecting step further comprises measuring the distance between each labeled target, to form a barcode representation of the polynucleotide, wherein the distances between the targets are represented.

In a preferred embodiment of the invention, the detecting step comprises using total internal reflection (TIR) microscopy and imaging fluorescence emission with a charge-coupled device (CCD) camera. In a further embodiment, the labels are fluorescent, and the detecting step comprises single-molecule high-resolution imaging with photobleaching (SHRImP). In yet a further embodiment, adjacent targets are separated by less than 1000 bases, the labels are fluorescent, and the detecting step comprises single-molecule high-resolution imaging with photobleaching (SHRImP).

DETAILED DESCRIPTION OF EMBODIMENTS OF THE INVENTION

Figure 1:
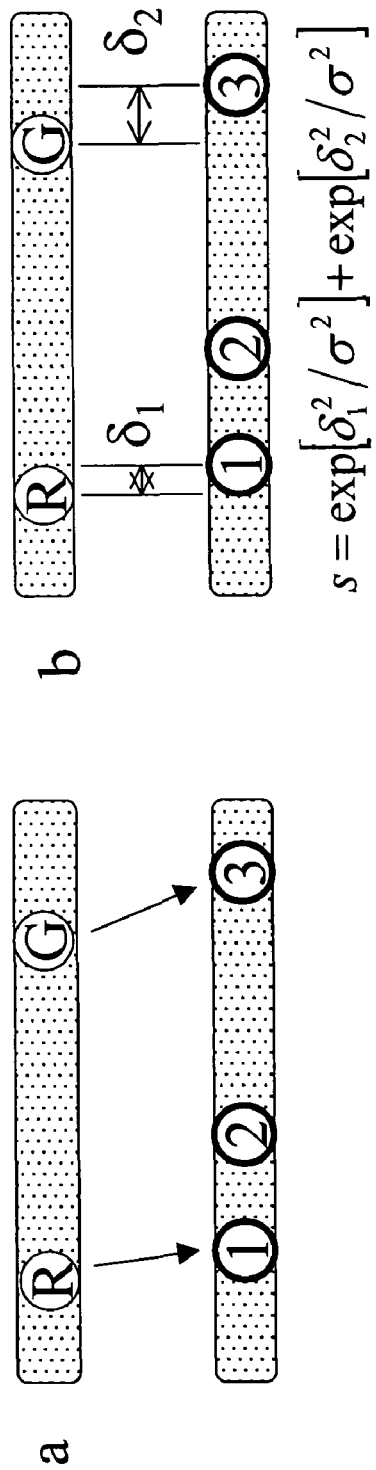
FIG. 1 Depicts an algorithm for determining haplotypes. (A) Each label is matched to one of the known loci based on position. (B) A score is computed for the fragment. (C) The score is added to the appropriate place in the score table.

One aspect of the invention is a method for barcoding a polynucleotide, comprising the steps of: a) immobilizing on a solid phase and stretching an isolated, individual polynucleotide comprising nucleotide targets; b) labeling each of the targets using a corresponding target-specific hybridization probe; and c) directly optically detecting an individual label of each said probe, unamplified, at each of the labeled targets, and determining their order to form a barcode representation of the polynucleotide wherein the targets and their relative positions are represented.

Typically, the polynucleotide to be barcoded is amplified from a sample of interest, such as a genomic DNA, cDNA, or mRNA sample. Long-range PCR is routinely used to amplify polynucleotide fragments in the 10-30 kb range. Thus, in one embodiment of the invention, the polynucleotide has a length of 10 to 30 kb. Some commercially available long-range PCR systems are capable of amplifying fragments up to 35 kb (e.g. Expand 20 kbPlus PCR System, Roche Diagnostics, Pleasanton, Calif.) and 50 kb (e.g. TripleMaster® PCR System, Brinkmann, Westbury, N.Y.). Thus, in certain embodiments of the invention, the polynucleotide has a length of up to 50 kb.

In one embodiment of the invention, the immobilizing and stretching step comprises a technique selected from the group consisting of viscous drag (Schwartz et al., Science (1993) 262:110; Houseal et al, Biophys. J. (1989) 56:507; Zimmerman and Cox, Nucleic Acids Res. (1994) 22:492; and Smith et al, Science (1992) 258:1122), electrophoresis (Smith et al, Science (1989) 243:203; Schwartz and Koval, Nature (1989) 338:520; Volkmuth and Austin, Nature (1992) 358:600; and Kabata et al., Science (1993) 262:1561), optical force (Chu, Science (1991) 253:861; Perkins et al, Science (1994) 264: 819; and Perkins et al, Science (1993) 262:822), and molecular combing (Bensimon et al, Science (1994) 265:2096-2098).

In a preferred embodiment of the invention, the immobilizing and stretching step encompasses molecular combing as used in genomic mapping studies (e.g. Michalet et al, 1997; and Conti and Bensimon, 2002) and analysis of gene rearrangements (e.g. Gad et al, 2002). The technique involves depositing a polynucleotide in solution onto a charged surface to which the polynucleotide will stick, such as glass functionalized with a silane compound, e.g. aminopropyl-triethoxy-silane (APTES). In one approach, as the solution dries, the moving meniscus of the evaporating fluid exerts a considerable force on the unstuck polynucleotide end as it passes, and causes the polynucleotide to be stretched out onto the glass surface by the moving fluid/air barrier. In another approach, the solution can be drawn between a silanized surface and a glass slide, which stretches the polynucleotide by capillary action. The surfaces are then separated and the fluid is allowed to evaporate (e.g. Jing et al, Genome Res (1999) 9:175-181).

The polynucleotide comprises nucleotide targets. Each of the targets is labeled using a corresponding target-specific hybridization probe which hybridizes to a subsequence of the polynucleotide encompassing the target. The probe and subsequence provide sufficient complementarity to effect target specificity. Preferred targets are variant across individuals, species, etc., such as SNPs. The immobilizing/stretching and labeling steps may be performed in either order. Thus, the targets may be hybridized with the probes before or after the immobilizing step.

Each hybridization probe comprises one or more individual labels that can be directly optically detected. Examples of labels that can be optically detected include fluorescent beads, quantum dots, fluorescent nanocrystals, and gold particles. In a preferred embodiment, the labels are selected from fluorescent labels and light-scattering labels. Examples of suitable fluorescent labels include fluorescein dyes such as 5-fluorescein (FITC), tetrachlorofluorescein (TET) and hexachlorofluorescein (HEX); green fluorescent proteins, particularly enhanced GFP (eGFP); rhodamine dyes such as tetramethylrhodamine (TMR), and carboxytetramethylrhodamine (TAMRA); Cy3 and Cy5; and Qdot® Nanocrystals (Quantum Dot Corp., Hayward, Calif.). Fluorescently-labeled nucleotides and custom probes are commercially available from a variety of vendors (e.g. Synthegen, Houston Tex.; Qiagen, Valencia, Calif.). Suitable light-scattering labels include metal nanoparticles, such as gold nanoparticles (Storhoff et al, Nat Biotechnol. (2004) 22:883-887), and colloidal silver plasmon-resonant particles (PRPs) (Schultz et al, Proc Natl Acad Sci USA (2000) 97:996-1001).

In a preferred embodiment, the labels are fluorescent, and comprise distinctly detectable fluorescent dyes. For example, one target may be labeled with Cy-3, which fluoresces yellow, and an adjacent target may be labeled with Cy-5, which fluoresces red. Fluorescent dyes may also be distinguished based on properties of the dye that impact on polarization observed such as dye lifetime, or net charge.

The label may be incorporated into the probe prior to target/probe hybridization, or after hybridization. The label may be directly bound to or incorporated in the probe, or it may be attached to the probe via a linker such as biotin-streptavidin. In one embodiment of the invention, the labels are fluorescent, are attached to the probes through different linkers, and in the detection step, the labels are distinguished based on different optical influences on the labels by the different linkers. In a further embodiment, the labels are fluorescent, are attached to the probes through different linkers, and in the detection step, the labels are distinguished based on different optical influences on the labels by the different linkers, wherein the linkers are different length carbon chains which polarize label fluorescence inversely to label length.

The probes used in the invention can be continuous or discontinuous. As an example of a discontinuous probe, one portion of a target is hybridized with one probe or probe portion, and another portion of the target is hybridized with another probe or probe portion, leaving a gap between the two hybridized probes or probe portions that is filled with one or more nucleotides. Thus, the probes also act as primers onto which one or more nucleotides are polymerized using the polynucleotide as a template. In one preferred embodiment of the invention, in the labeling step, discontinuous probes are hybridized to the targets, and gap-filled with fluorescent nucleotides. This approach works well when the targets are SNPs, and discontinuous probes are hybridized to the targets leaving a single nucleotide gap at the SNP position of each target. The probes are then gap-filled with labeled nucleotides, resulting in an individual label (e.g. a fluorescent nucleotide) of an unamplified probe (e.g. a circularized, gap-filled and nick-ligated, padlock probe) at each of the labeled targets. Because of the sensitivity of the method, probe and/or label amplification is unnecessary. The gap-filled approach can be particularly cost-effective when there are numerous targets because rather than labeling each probe, only the four nucleotides used for gap filling are labeled. In another preferred embodiment of the invention, in the labeling step, discontinuous probes are hybridized to the targets, and gap-filled with fluorescent nucleotides, wherein a first fluorophore is used to label a subset of nucleotides A, T, G, and C; and a second fluorophore is used to label the remaining nucleotides. In a further preferred embodiment of the invention, in the labeling step, discontinuous probes are hybridized to the targets, and gap-filled with fluorescent nucleotides, wherein a distinct fluorophore is used to label each of nucleotides, A, T, G, and C. Exemplary suitable four fluorophore combinations include Alexa dyes: Alexa 532, Alexa 594, Alexa 633, and Alexa 660; and Cy dyes: Cy3, Cy5, Cy5.5, and Cy7.

In a specific embodiment of the invention, the polynucleotide comprises SNP alleles of a haplotype, the targets are the alleles, and the barcode represents the haplotype.

The positions of three or more alleles may be analyzed and represented on the barcode, providing an advantage over methods where multiple analysis is required for haplotypes defined by more than two alleles (e.g. Goodwin et al, 2004). In a further embodiment of the invention, the polynucleotide comprises SNP alleles of a haplotype, the targets are the alleles, the barcode represents the haplotype, and the labeling step comprises using a distinct fluorophore to label each of a common and a minor polymorphism of each of the alleles.

In another preferred embodiment of the invention, in the labeling step, the probes are padlock probes (Nilsson et al, Science (1994) 265:2085-2088; Antson et al, Eur J Hum Genet. (2003) 11:357-363; and Antson et al, Nucleic Acids Res. (2000) 28:E58). When used to label an SNP, a 70-100 base pair probe is designed with ends that are complementary to flanking sequences on either side of the SNP and, depending on whether the "labeled probe" or "gap-filled" (i.e. discontinuous probe) approach is used, either 1) has one of two possible bases in the SNP position, or 2) has no base in the SNP position leaving a gap at the SNP position, respectively. In the labeled probe approach, the probe is labeled with a molecule that can be optically detected. For example, after target hybridization, the probe can be labeled via a label-attached oligonucleotide that specifically hybridizes to a portion of the padlock probe sequence between the ends. Optionally, the padlock probe may be pre-labeled and then hybridized to the target. In the gap-filled approach, after hybridization, labeled nucleotides are added, and in the presence of DNA polymerase and DNA ligase, the appropriate complementary nucleotide hybridizes to the SNP, the nicks at the probe ends are ligated, and unhybridized probes are removed by stringent wash.

In large-scale haplotyping studies, it becomes necessary to differentiate DNA fragments from different regions of the genome, and haplotype fragments from many regions simultaneously. In order to differentiate regions, PCR primers for different regions can be differentially labeled so that fragments derived from different regions will be distinguishable by the label at the end of the fragment. This can be achieved by labeling with multiplexed quantum dots (Xu et al, Nucleic Acids Res (2003) 31:e43-43) or organic dyes that can be differentiated from each other by fluorescence lifetime as well as color (Clegg et al, SPIE (1994) 137:105-118). Thus, in one embodiment of the invention, the method further comprises the step of end-labeling the polynucleotide.

In addition to labeling the targets, the polynucleotide can be labeled with a sequence non-specific dye which allows visualization of the polynucleotide during the detection step, and facilitates measuring the distances between individual labels. Thus, in a preferred embodiment of the invention, the method additionally comprises, prior to the detecting step, labeling the polynucleotide with a sequence non-specific dye. Examples of sequence non-specific dyes that can be used includes 7-aminoactinomycin D (7-AAD), acridine orange, bisbenzimide, BOBO-1, BOBO-3, chromomycin A3, DAPI, ethidium bromide, Hoechst 33258, Hoechst 33342, Hoescht 33245, LDS 751, mithramycin, propidium iodide (PI), pyronine, SYTOX Blue, SYTOX Green, SYTOX Orange, TO-PRO-1, TOTO-1, TOTO-3, YOYO-1, and YOYO-3. Presently preferred dyes are YOYO-1™ and BOBO-1™. In a further preferred embodiment of the invention the method additionally comprises, prior to the detecting step, labeling the polynucleotide with a sequence non-specific dye, and the detecting step comprises determining the ratio of intensity of the dye on one side of a labeled target to the total dye intensity to provide a position of the labeled target as a fraction of the total length of the polynucleotide. Using this method, we can measure the distance between each labeled target. Thus, in a further preferred embodiment of the invention, the detecting step further comprises measuring the distance between each labeled target, to form a barcode representation of the polynucleotide, wherein the distances between the targets are represented.

In another embodiment of the invention, in the detecting step, the predetermined number is from 1 to 8, preferably from 1 to 4. The label number is independent of probe length. In a particular embodiment, the number is one, i.e. a single, individual label of each probe is directly, optically detected, such as with FIONA.

Optical detection of individual labels can be achieved by a variety of methods including near-field scanning optical microscopy (Dunn, Chem Rev. (1999) 99:2891-2928), total internal reflection (TIR) microscopy (Axelrod, Methods Cell Biol. (1989) 30:245-270), and dark-field microscopy (Schultz et al, 2000). In one preferred embodiment of the invention, the detecting step comprises using TIR microscopy and imaging fluorescence emission with a charge-coupled device (CCD) camera (Yildiz, 2003). Using this method detection of high density nucleotide targets, such as closely-spaced SNPs separated from each other by less than 1000 bases can be achieved. A single dye molecule is illuminated by total internal reflection and the photons emitted by the dye molecule are collected by a high-numerical aperture oil objective, and imaged using a high-speed back-thinned cooled CCD camera. The image of a single fluorescent molecule (often called its "point spread function", or PSF) will have a width (w), dictated by the Rayleigh diffraction limit, of $\lambda(2\times NA)$, where $\lambda$ is the wavelength of the emitted light, and NA is the numerical aperture of the optical system. In a technique we refer to as Single-molecule High Resolution Imaging with Photobleaching (SHRIMP), two overlapping PSFs are imaged continuously until one of them photobleaches. We can then use the image of the remaining PSF, combined with the image of both PSFs from before the photobleach, to determine the distance between the two PSFs. Each image frame is fit to a Gaussian distribution to determine the position of the centroid of the PSF. Using SHRIMP, we have been able to resolve distances between single dye molecules down to 10 nm (Gordon, 2004). Thus, in one preferred embodiment of the invention, in the labeling step, adjacent targets are labeled with fluorophores, and the detecting step comprises single-molecule high-resolution imaging with photobleaching (SHRImP). In a further preferred embodiment of the invention, adjacent targets are separated by less than 1000 bases, the labels are fluorescent, and the detecting step comprises single-molecule high-resolution imaging with photobleaching (SHRImP).

The invention further provides kits for barcoding a polynucleotide. The kits generally comprise reagents as described above for practicing the methods of the invention. The reagents are premeasured, separately packaged and labeled, and are preferably accompanied with instructional material on how the reagents are used to practice disclosed methods, e.g. comprising the steps of: a) immobilizing on a solid phase and stretching an isolated, individual polynucleotide comprising nucleotide targets; b) labeling each of the targets using a corresponding target-specific hybridization probe; and c) directly optically detecting an individual label of each unamplified probe at each of the targets, and determining label order to form a barcode representation of the polynucleotide wherein the targets and their relative positions are represented. In one embodiment, the kit comprises premeasured, separately packaged and labeled amounts fluorescent nucleotides, particularly four differentially detectable nucleotides A, T, C and G for incorporation into gap-filled probes as disclosed herein. The kit may optionally include a solid phase device for immobilizing and stretching isolated polynucleotides as describe herein.

EXAMPLES

Specific Aspects of the Invention. In one aspect, the invention provides a system for high-throughput haplotyping of individuals and populations. Many companies, including Affymetrix (e.g. Matsuzaki, et al. (2004) Genome Research 14, 1444-1444), ABI (e.g. De La Vega, et al. (2002) Biotechniques, 48-50, 52, 54.), Illumina (e.g. Oliphant, et al. (2002) Biotechniques, 56-8, 60-1), ParAllele (e.g. Hardenbol, et al. (2003) Nature Biotechnology 21, 673-678), and Perlegen (e.g. Patil, et al. (2001) Science 294, 1719-23) have developed cost-effective techniques for high-throughput genotyping of single-nucleotide polymorphisms (SNPs). These techniques are valuable for large-scale, genome-wide association studies. But, after genomic regions of potential interest have been identified, the measurements must be repeated at higher resolution over smaller regions in order to confirm the associations detected by the large-scale studies and to narrow down the region that will be sequenced exhaustively in cases and controls to identify the causative variants. The SNP genotyping techniques cited above are not well suited for this purpose, because the cost does not scale well for higher-resolution studies of smaller numbers of markers. Additionally, these techniques cannot determine the haplotype of polyallelic loci in diploid organisms such as mammals, and are therefore unable to take advantage of haplotype analysis, which has much more predictive power than analyzing SNPs alone, at this critical phase of a genetic association study. Our invention provides a cost-effective, high-throughput system for haplotyping based on single-molecule technologies.

Our invention integrates several single-molecule technologies for single-molecule genotyping. In one aspect, we combine molecular combing to stretch individual DNA molecules, padlock probes for allele-specific fluorescent labeling of PCR products, and FIONA for high-resolution localization of single fluorescent dye molecules in order to generate "barcoded" DNA fragments from which we read the genotype of individual DNA molecules. We include various methods of padlock probe labeling and DNA mounting, systems for cleaning and functionalizing glass coverslips for DNA mounting, different DNA backbone dyes and padlock probe dyes, and adapting single-molecule imaging conditions to established DNA mounting conditions. Our invention also provides algorithms for analyzing images and co-localizing DNA backbone images with single dye molecules.

Our invention permits single-molecule haplotyping of a diploid sample and heterozygous human samples using data analysis and algorithms that can detect multiple haplotypes (e.g. two) in a population, using improved labeling efficiency, labeling specificity, and DNA mounting.

Our invention provides large-scale haplotyping of multiple individuals by generating haplotypes of a biologically relevant region (such as a 500 kb ENCODE region containing the HOXA locus on human chromosome 7, as part of the ongoing work of the International HapMap consortium) for a statistically significant number of individuals (e.g. about 100). This aspect is performed by automating the imaging, data collection, and data analysis steps, including integrating an automated microscope, nanometric positioning stage, total-internal reflection illuminator, and slow-scan back-thinned CCD camera. It also employs image analysis software for extracting relevant DNA fragments and automatically analyzing and categorizing them by haplotype. In addition, by uniquely tagging DNA fragments from different regions using unique multiplexed markers, we can examine multiple regions simultaneously, and differentiate them by their tag, dramatically reducing the time required to completely characterize an individual's haplotype. Further, by haplotyping multiple overlapping regions, we are able to extend associations beyond the limitations imposed by long-range PCR, which is currently limited to approximately 20 kilobase fragments.

Our invention extends to population haplotyping, enabling rapid large-scale association studies of hundreds of individuals simultaneously by combining an entire population's DNA into a single sample and detecting the frequency of all the haplotypes present simultaneously. This technique reduces the amount of time required to characterize the haplotypes of a population, and facilitates gene association studies by allowing large-scale gene association studies on a statistically significant population to be performed in weeks instead of months or years.

Examples of Specific Aspects of the Invention. The premise underlying the field of genomics is that physiological conditions of medical and scientific interest can be correlated with genetic variation. While this has been demonstrated amply for simple, Mendelian disorders, multifactorial diseases such as obesity and hypertension are resistant to such approaches. This is primarily because of the complex pattern of inheritance and the fact that environmental factors play a major role in disease penetrance. With the successful elucidation of the human genome sequence and the construction of high-density genetic maps, the stage is set for genetic association studies to identify the genetic determinants of complex human diseases. However, a major technical limitation in genetic association studies is that the existing technology is limited to resolving single nucleotide polymorphisms (SNPs), and cannot resolve alleles expressed at each SNP on each chromosome (the haplotype) of heterozygous individuals, because they cannot differentiate DNA from different chromosomes.

In one aspect, our invention provides resolution of genetic haplotypes by observing allele-specific labeling of single DNA molecules by combining Fluorescence Imaging with One Nanometer Accuracy (FIONA), molecular combing, and padlock probe labeling; thus, observing DNA haplotypes at the single molecule level. Our technology fills a much needed gap in the process of gene association studies, because there is currently no other way to quickly and accurately haplotype individuals once regions of interest in the genome have been established using already existing SNP genotyping technologies.

In various embodiments, 1) we use three-color single molecule imaging to to determine the haplotype of single 10 kilobase PCR fragments. We do this by labeling specific SNPs with different colors in an allele-specific fashion. We then label the DNA with a backbone-specific dye such as YOYO, and then stretch the fragments using fluid flow onto a functionalized glass surface. We then image all three colors and overlay the images to generate "barcoded" DNA fragments from which we determine the haplotype. 2) We take samples of interest to the international HapMap consortium and resolve the haplotype of both chromosomes of heterozygous individuals. We can distinguish two populations of molecules with different haplotypes because we examine single DNA molecules one at a time. 3) We automate our data collection and data analysis systems, and end-tag fragments from different regions, so that we can analyze multiple regions simultaneously. We can analyze a statistically significant number of samples (approximately 100 individuals) to determine haplotypes for the HapMap consortium. 4) We haplotype multiple individuals simultaneously. Since our technique establishes haplotypes based on single molecules, it is inherently capable of distinguishing multiple populations. The ability to haplotype entire populations in a massively paralleled fashion improves gene association studies by decreasing the amount of time and money required to perform such studies. Further, this technology has application to other areas of genomics, including mRNA quantification and determination of mRNA splicing variants.

Padlock Probe Labeling. To demonstrate the specificity of the padlock probe labeling system, a 9.3 kbp region of genetic DNA was chosen with four known SNPs, and two individuals were identified both of whom are homozygous at all four SNPs. PCR products were obtained for each individual, and three experiments were performed on each sample. In each experiment, probes for all four positions were introduced into the sample, but only one of them had the correct complementary base at the SNP position. The probes were then hybridized to the PCR products and circularized using DNA ligase. The expectation is that only the probe with the correct base pairing would be circularized, and the other three would not. Following this procedure, the circularized probes were amplified by PCR and sequenced. The result in each case was that only one probe was found to be present in the PCR products, and sequencing showed that the probe that was present was the one that had been correctly base paired with its SNP.

To determine labeling efficiency, we used 9.3 kbp fragments which had four labeled positions, which we backbone labeled and imaged. If there are N label positions, the labeling efficiency is the same for each position, and if the probability of labeling any position is position is p, then the probability of observing n labels is $_NC_n p^n(1-p)^{N-n}$, where $_NC_n$ is the binomial coefficient "N choose n". Using this expression, we can compute the expected probability of observing a singly labeled fragment or a doubly labeled fragment, and thence the ratio of these probabilities. By inverting this expression, we can then compute the labeling efficiency from the observed ratio of doubly labeled to triply labeled fragments, for example, or singly labeled to doubly labeled fragments. This method of computing labeling efficiency reduces the errors due to photobleaching and uneven sample illumination, and allows us to cross-check the value in several ways. We have found that the labeling efficiency is approximately 50% on most of these preliminary samples. At this labeling efficiency, with four label positions, we would expect 6.25% of fragments to be fully labeled, which agrees with our observations. This level of labeling efficiency is sufficient to determine haplotypes.

FIONA. For these studies, we used a conventional epifluorescence microscope configured for object-type total-internal reflection microscopy (TIRM), which significantly reduces the background fluorescence due to molecules not close to the coverslip. Our model system for proof-of-principle measurements consisted of a Cy3 dye covalently attached to a biotinylated DNA immobilized onto a coverslip via a streptavidin-BSA complex. The DNA is placed on the coverslip at a density <<1 dye/μm², sufficiently sparse such that the dyes are well separated from each other, and yet many spots are present in the excitation area. TIR excitation results in dye emission, and several spots can be simultaneously imaged and recorded on a sensitive CCD. The intensity difference between spots is due to non-uniform illumination. We used a back thinned (quantum yield 90%) frame-transfer camera which is capable of taking full frame images with no deadtime between images at a rate of 3 frames/sec, or an image time of approximately 0.33 sec. The image of a small punctate object—the PSF—is an Airy pattern. One data image shows an expanded view of one peak, overlaid with a curve fit to a 2-dimensional Gaussian. Examining the residuals between the curve fit and data, we find the fit is excellent ($r^2$=0.994). In the residuals graph, a slight ring could be seen—this is the expected difference between an Airy pattern and a Gaussian fit. The center of the PSF can be determined with a precision of 1.2 nm by fitting to a Gaussian function. Furthermore, use of oxygen scavenging systems, such as glucose oxidase and catalase (e.g. Harada et al., J. Mol Biol (1990) 216:49), or reductants such as beta-mercaptoethanol, provide conditions that lead to highly stable fluorescence of single Cy3 molecules, with very little blinking, and fluorescence which often lasts several minutes.

These capabilities exceed what is required for our observation of static molecules. Our requirements for time resolution and dye lifetime are that we be able to image for long enough that we can collect enough photons to accurately localize the labels, and that we can do so quickly enough that we can achieve high throughput data collection. Furthermore, we need only be able to localize dyes to within several hundred base pairs, as SNPs are typically separated by over 1000 bases. Assuming the DNA is stretched on the surface at approximately 0.25 to 0.35 nm/base pair, this corresponds to at the very minimum 25-35 nm, which is easily within the accuracy available to us. Under these constraints, imaging each color for several seconds is practical, and provides us with an excess in the number of photons required for accurate localization.

Single-molecule High Resolution Imaging with Photobleaching (SHRIMP). As we haplotype a higher density of SNPs in a given region, it is necessary to determine the relative positions of dye molecules which are closer together. However, because the PSF is approximately half a wavelength in width, the Rayleigh criterion suggests that we cannot resolve individual molecules of the same color which are closer together than about 250 nm, because their PSFs begin to overlap too much.

To circumvent this limitation, we have developed a method which allows us to resolve the distance between single dye molecules of the same color which are separated by as little as 10 nm (Gordon, et al. (2004) PNAS 101, 6462-6465). In this technique, which we call Single-molecule High Resolution Imaging with Photobleaching (SHRIMP), two overlapping PSFs are imaged continuously until one of them photobleaches. We can then use the image of the remaining PSF, combined with the image of both PSFs from before the photobleach, to determine the distance between the two PSFs. To test this, we took DNA oligos of 30, 40, and 50 base pairs, labeled at each end with a Cy3 molecule, and made ~50 distance measurements of each. We were able to determine the correct length of the oligos, with a standard deviation of about 5 nm. This technique is already being used for high-resolution DNA mapping using PNA probes (Qu, et al. (2004) PNAS, 0402155101).

Molecular Combing. We used an established protocol (Jing, et al. (1998) Proc Natl Acad Sci USA 95, 8046-8051) for acid-cleaning coverslips, and for functionalizing and mounting DNA by incubating them in a mixture of trimethylsilane and vinylsilane. Finally, we took our 9.3 kbp DNA fragments, and mounted and labeled these with YOYO-1-iodide. Imaging revealed that the DNA fragments are well separated and well stretched. There is very little background, and we observe no degradation of the mounted DNA over the course of an hour. Slides prepared as disclosed should remain usable for several days.

Two Color DNA Labeling. Our first goal in combining these techniques was to establish a system, including a backbone dye, padlock probe label, and imaging system, which would allow two-color and three-color labeling of DNA: one color for backbone labeling, and two for allele-specific padlock probe labeling. Our microscope configuration allows illumination with up to two laser lines and a mercury lamp. We use the laser lines to illuminate the padlock probe labels, and the mercury lamp to illuminate the DNA backbone label, since the backbone imaging, which involves many dye molecules per DNA molecule, has a much higher signal to noise ratio than imaging single dye molecules.

Because our work on FIONA with Cy3 was very successful, we decided to continue with Cy3 as the padlock probe label. And, because of the similarity of the Cy3 spectrum to that of tetramethylrhodamine (TMR), we would retain the ability to experiment with TMR as well in later stages, to reduce the cost of a potential large-scale assay.

Working with Cy3 as the probe label, we demonstrated feasibility with two different systems. The first uses BOBO-1 as a backbone label, with mercury lamp illumination at 436 nm, and Cy3 illumination from a 532 nm diode-pumped YAG laser. The 532 nm diode-pumped YAG is a popular laser for OEM biotech applications, because of its compact footprint and high power. The second system uses YOYO-1 for backbone labeling, with mercury lamp illumination at 488 nm, and a 543 nm HeNe laser for Cy3 illumination. Our experiments showed that YOYO-1 is superior to BOBO-1 in terms of brightness, evenness of labeling, and photostability, and that labeling with YOYO-1 results in 15% better stretching of DNA. However, the excitation spectrum of YOYO-1 has greater overlap with Cy3 than does that of BOBO-1, and due to the extremely dense backbone labeling, it contributes to a significant level of background in the Cy3 image channel if 532 nm is used for illumination. Shifting the Cy3 excitation down to 543 nm solves this problem easily, but the 543 nm HeNe is not as convenient because of its lower output power, and because of the wider availability of the diode-pumped YAG.

We then tested whether we could accurately localize a single label to a specific position on the DNA backbone. First we developed algorithms for picking DNA fragments from an image and for computing the backbone contour of extracted fragments. The former can be achieved easily using well-known image processing techniques such as image segmenting and eccentricity. We computed DNA contours with a contour extraction algorithm. We start with a magnified image of a YOYO-labeled DNA fragment, wherein each line of pixels along one axis is a cross-section of intensity through the DNA fragment. Each of these is fit to a one-dimensional Gaussian, and the centroid of each Gaussian forms one point on the DNA backbone contour. In this example, the intensity along the backbone was not uniformly distributed, because the stretching of the DNA along its length was not uniform. So, in order to determine the position of a point along the DNA length in terms of the number of base pairs, or the fraction of the whole DNA length, we split the DNA contour at that point, and take the ratio of intensity on one side of the point to the total intensity. This gives us the position of the point as a fraction of the total length of the DNA fragment.

To test the system, we took a 9.3 kbp fragment, which was labeled with a single Cy3 dye at a position 900 bp from one end. We found that approximately 50% of the fragments were labeled, and measured the position of the label on approximately 40 fragments. We measured the position at 716±63 bp, within 200 bp of the known position. Compared to the resolution available from flow-based systems of approximately 2 kbp (Chan, et al. (2004) Genome Research 14, 1137-1146), this is excellent, and more than adequate for our purposes. In another experiment, we localized the dye on a labeled fragment at 3377±163 bp compared to the known position of 3241 bp from one end. Yet another example presents a contour map and false color image of a 20 kbp DNA fragment that has been covalently labeled at both ends, and has a padlock probe at a position 3 kbp from one end.

Three Color DNA Labeling and Haplotyping. Our next step was to demonstrate that we could add a third color, image the backbone and both label colors, and use this system to establish the haplotype of a an individual. A 9.3 kbp fragment from a homozygous individual with a known haplotype was used to test the system. Padlock probes were designed to label specific loci such that if a particular allele was present it would be labeled with a Cy3, or if an alterative allele was present, it would be labeled with a Cy5. We also modified our imaging system to enable us to detect both labels by adding a 633 nm HeNe in parallel with the 532 nm diode-pumped YAG, and utilizing a dual-band dichroic and dual-band-pass emission filter. Each laser has its own shutter, allowing us to take three sequential images, one of each label color, and one of the DNA backbone, which can then be merged into a single three-channel image for analysis. We used BOBO-1 for backbone labeling, and changed our mercury lamp excitation filter to pass 436 nm, which more efficiently excites BOBO-1.

In these experiments, we tested the Olympus TIRFM fiber illuminator as a laser illumination source. The Olympus TIRFM illuminator is a turn-key solution for performing total internal reflection (TIR) illumination which has some advantages, such as a very large and highly uniform illumination area. While these are desirable properties, the low intensity throughput of the fiber coupling and illuminator make it less attractive to use with a low-power laser such as the 543 nm HeNe laser. Having extensive experience in our lab with TIR optics, we found the Olympus solution to be in fact less convenient to use because of the difficulty of achieving adequate fiber coupling, the inconvenient interface for aligning the fiber launch with the illuminator, and the sacrifice in flexibility that one must make in using a off-the-shelf solution. Nevertheless, this may be a valuable approach for making this technique widely available to practitioners with less optics expertise, and we certainly found it to be adequate for these purposes.

We extracted fragments, computed their contours, and determined the position of each label on the backbone as discussed above, and this data is logged for later analysis. With labeling efficiency of about 50%, for a fragment with four labeled positions, a fraction of observed molecules have all four positions labeled (approximately $0.5^4$=6.25%). So, it is desirable to have an algorithm that can take advantage of data points that are not fully labeled, but can make contributions to determining the complete haplotype. Our algorithm is described below, and illustrated in FIG. 1. In the description that follows, individual alleles will be referred to as either red (R) or green (G), since this is how they are viewed by the algorithm. The correspondence between label color and actual allele is trivial, since there is only a single probe for each color which corresponds to each allele at a given position.

The first task is determining the orientation of the fragment (since there is a two-fold degeneracy), and determining which label corresponds to which position (FIG. 1a). We know in advance where we expect the labels to be, because we have chosen to label SNPs with known positions. Call these positions $x_i$. We examine fragments that have at least two labels, and we know the position of each label, which we will call $p_i$.

We then generate every possible pairing between labels and positions, including those achieved by reversing the fragment orientation, within the constraint that the labels must be assigned in a manner consistent with their observed linear ordering.

Now, for each allowed pairing, we generate a score as follows: for each label $x_i$ which has been assigned to a position $p_{x_i}$, we compute the score $s=\exp[-(x_i-p_{x_i})^2/\sigma^2]$, where $\sigma$ is an estimate of the standard deviation of the position measurements. The score for the pairing is then the sum over all i, giving a score S (FIG. 1b). The pairing with the highest score is chosen as the correct one. So, at this point, we have taken a fragment with a number of dyes on it, determined which dye corresponds to which locus, and assigned a score to how well this fragment fits the expected "template."

To determine the haplotype of the sample, we keep a table of running scores (FIG. 1c): for each locus, we have a green score, and a red score. When we analyze a fragment as described above, we assign each observed dye to a particular locus. For each locus on each fragment, if a green dye is observed, we add the fragment score to the green column, and vice versa for red. If no dye is assigned to a particular locus, we add nothing to that column. Additionally, scores from fragments with more labels are weighted more heavily than those with fewer labels, because we expect to be able to determine the label-to-locus pairing with greater certainty for these fragments. Iterating over all the observed fragments, we get two scores for each locus, one for red, and one for green. The color with the higher score is the predicted allele at that locus.

We examined a homozygous sample, with the haplotype green-red-red-green, dubbed A8. We examined 49 fragments that had at least three labels, and scored them. Imaging showed one of a small number of fully-labeled 4-dye fragments, which shows the expected haplotype, green-red-red-green. The results of computing haplotype scores for each position based on all 49 fragments reveal a consensus haplotype green-red-red-green, as expected.

The algorithm demonstrated above can be easily applied to heterozygous samples, or multiple samples, by scoring entire haplotypes instead of individual positions: any multiply-labeled fragment may be considered as evidence for a subset of haplotypes. If a particular fragment shows, for instance, RG*R, where the * represents a position with no label, then the haplotypes RGGR and RGRR are scored positively. After scoring many fragments, the haplotypes will be ranked according to score, with the more prevalent haplotypes ranked higher.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for barcoding a polynucleotide, comprising the steps of:
   a) immobilizing on a solid phase and stretching an isolated, individual polynucleotide comprising nucleotide targets;
   b) labeling each of the targets using a corresponding target-specific hybridization probe; and
   c) directly optically detecting a single, individual fluorescent label of each unamplified probe at each of the targets, and determining label order to form a barcode representation of the polynucleotide wherein the targets and their relative positions are represented,
   wherein in the labeling step, discontinuous padlock probes are hybridized to the targets, and gap-filled with fluorescent nucleotides.

2. The method of claim 1 wherein in the labeling step, discontinuous padlock probes are hybridized to the targets, and gap-filled with fluorescent nucleotides, and wherein a first fluorophore is used to label a subset of nucleotides A, T, G, and C; and a second fluorophore is used to label the remaining nucleotides.

3. The method of claim 1 wherein in the labeling step, discontinuous padlock probes are hybridized to the targets and gap-filled with fluorescent nucleotides, and wherein a distinct fluorophore is used to label each of nucleotides, A, T, G, and C.

4. The method of claim 1 wherein the polynucleotide comprises SNP alleles of a haplotype, the targets are the alleles, and the barcode represents the haplotype.

5. The method of claim 1 wherein the polynucleotide comprises SNP alleles of a haplotype, the targets are the alleles, the barcode represents the haplotype, and wherein the labeling step comprises using a distinct fluorophore to label each of a common and a minor polymorphism of each of the alleles.

6. The method of claim 1 further comprising the step of end-labeling the polynucleotide.

7. The method of claim 1 additionally comprising, prior to the detecting step, labeling the polynucleotide with a sequence non-specific dye.

8. The method of claim 1 additionally comprising, prior to the detecting step, labeling the polynucleotide with a sequence non-specific dye, wherein the detecting step comprises determining the ratio of intensity of the dye on one side of a labeled target to the total dye intensity to provide a position of the labeled target as a fraction of the total length of the polynucleotide.

9. The method of claim 1 wherein the detecting step further comprises measuring the distance between each labeled target, to form a barcode representation of the polynucleotide, wherein the distances between the targets are represented.

10. The method of claim 1 wherein the detecting step comprises using total internal reflection (TIR) microscopy and imaging fluorescence emission with a charge-coupled device (CCD) camera.

11. The method of claim 1 wherein the detecting step comprises Fluorescence Imaging with One Nanometer Accuracy (FIONA).

12. The method of claim 1 wherein the detecting step comprises single-molecule high-resolution imaging with photobleaching (SHRImP).

13. The method of claim 1 wherein adjacent targets are separated by less than 1000 bases, and wherein the detecting step comprises single-molecule high-resolution imaging with photobleaching (SHRImP).

* * * * *